United States Patent [19]

Ackelsberg

[11] Patent Number: 5,212,737
[45] Date of Patent: May 18, 1993

[54] REAL TIME DATA AVERAGER FOR USE IN COMPUTED TOMOGRAPHY SCANNING

[75] Inventor: Sholom M. Ackelsberg, San Francisco, Calif.

[73] Assignee: Imatron, Inc., So. San Francisco, Calif.

[21] Appl. No.: 767,505

[22] Filed: Sep. 30, 1991

[51] Int. Cl.$^5$ .............................................. G06K 9/00
[52] U.S. Cl. ................................... 382/6; 364/413.14; 364/413.19; 378/21; 382/54
[58] Field of Search .................. 382/6, 54, 62; 378/21, 378/24; 364/413.13, 413.14, 413.15, 413.16, 413.18, 413.19; 358/111

[56] References Cited

U.S. PATENT DOCUMENTS

| | | | |
|---|---|---|---|
| 4,259,721 | 3/1981 | Kuznia | 382/54 |
| 4,335,427 | 6/1982 | Hunt et al. | 382/54 |
| 4,430,749 | 2/1984 | Schardt | 382/6 |
| 4,630,202 | 12/1986 | Mori | 382/6 |
| 4,789,929 | 12/1988 | Nishimura et al. | 382/6 |
| 4,868,747 | 9/1989 | Mori et al. | 382/6 |
| 5,034,987 | 7/1991 | Fujimoto et al. | 382/413.14 |
| 5,123,059 | 6/1992 | Wilson | 382/6 |

*Primary Examiner*—Joseph Mancuso
*Attorney, Agent, or Firm*—Flehr, Hohbach, Test, Albritton & Herbert

[57] ABSTRACT

A helical CT scanning system includes a real time averager that rapidly processes data from the system's detector array, to enable substantially real time production of X-ray images. The averager, which may be used with an scanning electron beam CT system operating in conventional or helical mode, or with a rotating mechanical gantry CT scanner operated in conventional or helical mode, includes an adder and first and second memory banks and an input FIFO register. The FIFO register synchronously communicates system detector array data to the adder. The adder combines this input data with data previously stored in one of the memory banks. For example, after a first X-ray scan, detector data are written via the FIFO and adder into the first data bank, and after a subsequent scan, the sum of the original data in the first data bank is added to the new data corresponding to the second scan, and the new summation is written into the second data bank. After a third scan, new data corresponding to the third scan is added to the data in the second data bank and the new summation is written into the first data bank, and so on. The data in the most recently acquired data bank is divided by the number of scans per resultant image (N) to provide a running real time or "on the fly" average value of data per scan.

9 Claims, 6 Drawing Sheets

REAL TIME DATA AVERAGER FOR USE IN COMPUTED TOMOGRAPHY SCANNING

FIELD OF THE INVENTION

The present invention relates generally to data processing systems used with computed tomography (hereafter "CT") X-ray transmission system, and more particularly to a system for real time data averaging in a scanning electron beam computed tomography X-ray system, including a helically scanned system.

BACKGROUND OF THE INVENTION

Computed tomography scanner systems can be implemented using a mechanically rotated gantry, or more recently, using a scanning electron beam. Either system may be operated in a conventional mode (e.g., non-helical) or, more recently, in a helical mode. Mechanically rotated gantry CT systems and their helical mode operation are described in U.S. Pat. No. 4,630,202 (Mori), issued Dec. 16, 1986. Scanning electron beam CT systems and their conventional mode operation are described in U.S. Pat. No. 4,352,021 (Boyd, et al.), issued Sep. 28, 1982, and in U.S. Pat. No. 4,521,900 (Rand), issued Jun. 4, 1985. Applicant refers to and incorporates by reference herein said patents to Mori, Boyd, et al. and Rand.

While the present invention is primarily directed to real time averaging of data acquired during helical mode operation of a scanning electron beam CT system, it is useful to review the problems attendant first with conventional mode operation of both types of CT systems, and then with helical mode operations.

In a mechanically rotating gantry CT system, an X-ray tube and an X-ray detector are located diametrically opposite from each other within a large doughnut shaped rotatable gantry. The patient or object to be X-rayed is positioned within the gantry opening and the gantry is mechanically rotated about the patient's lateral axis to scan an image slice. The X-ray detector signals are computer processed to produce images of the X-rayed patient. In conventional mode operation, the patient is stationary and a typically 360° gantry scan is made, after which the patient is moved laterally a few mm and held stationary while a second scan is made, and so forth. Typically each lateral repositioning of the patient takes about one second, and each 360° mechanical rotation of the gantry takes another second. The patient is moved laterally between scans a distance typically corresponding to the acquired image slice width (e.g., typically about 1 mm to about 10 mm). In conventional mode operation, the image slice width capability of the system (whether mechanical gantry or scanning electron beam) is a function of the system geometry and is not determined by the patient's lateral movement.

In a mechanically rotating gantry CT system operating in helical mode, the patient moves continuously laterally while scans are made at the rate of one scan/second. Because there is no one second dead time while the patient is laterally repositioned, scanning in helical mode is clearly faster than conventional mode. In helical mode operation, the image slice width is determined by the patient's lateral movement.

Briefly, mechanical gantry scanners have several intrinsic limitations, regardless of their mode of operation. First, because scanning is accomplished by mechanically rotating the gantry, scanning is intrinsically slow, requiring about one second/rotation. Second, heat dissipation associated with the scanning process occurs within the X-ray tube itself, and X-ray current is limited to about 125 mA. Finally, after about 30 seconds of continuous scanning, the X-ray tube must be turned off and allowed to cool, a severe limitation where multiple scan cycles are required to scan a large volume of a subject.

In a scanning electron beam system, such as described in U.S. Pat. No. 4,521,900 to Rand, an electron beam is produced by an electron gun and is accelerated downstream along the Z-axis of an evacuated chamber. Further downstream a beam optical system deflects the electron beam into a scanning path, typically about 210°. The deflected beam is then focussed upon a suitable target, typically a large arc of tungsten material, which produces a fan beam of X-rays. The X-rays penetrate an object (e.g., a patient) and are then detected and computer processed to produce an X-ray image of a slice of the object.

In conventional mode use, lateral positioning of the patient takes about one second, after which a typical 210° scan is accomplished in about 0.05 seconds or about 0.10 seconds, as selected by the X-ray practitioner operating the system. This rapid scan time results because the electron beam is scanned by magnetic deflection, rather than by mechanical rotation.

In brief, a scanning electron beam system has several intrinsic advantages over a mechanical gantry system. Not only is the scan time considerably faster (e.g., 0.05 seconds to 0.10 seconds compared to about 1 second), but because heat dissipation occurs in the large target ring, a relatively high beam current can be used (e.g., about 1,000 mA compared to about 125 mA). Finally, a scanning electron beam system can be continuously operated for about one minute before scanning must be interrupted to permit cooling.

In any X-ray system, a relatively rapid scan repetition rate is preferred providing certain minimum X-ray dosage requirements are met. Often the patient ingests or is injected with an iodine medium to enhance contrast in the X-ray image to be produced. A relatively slow scan repetition rate means a large dose of medium must be used so that some medium will remain active near the end of the scanning session. Unfortunately the medium is expensive and, in large dosage, unpleasantly invasive to the patient. Further, a slow scanning repetition rate means image quality may be impaired by organ functions. Overall, a slow scan repetition rate means fewer patients can be examined within a given time, thus representing an inefficient use of the CT X-ray facility.

The X-ray current or electron beam current associated with a system can also be an important system limitation because the object being examined will attenuate or absorb the X-rays. As is well known to those skilled in the art of imaging physics, there must be at least a minimum X-ray dose to successfully image a particular object with minimal photon noise. A successful image slice of an object requires an X-ray dosage defined as the product of the X-ray or electron beam current multiplied by the X-ray exposure time duration, commonly referred to as milliampere-seconds, or "mAs". For example, to image a human skull requires an X-ray dosage of about 800 mAs/slice, a human abdomen typically requires about 250 mAs/slice, and a human chest typically requires about 150 mAs/slice.

Consider for example a scan of a human abdomen with a mechanical gantry system in helical mode. Because the mechanical gantry system is limited to 125 mA X-ray current, the requisite 250 mAs dosage to acquire data for an adequate image slice of the abdomen is equivalent to a 125 mA X-ray current for an exposure of two seconds, e.g., 2 seconds per slice of about 10 mm, a "pitch" of 2:1. Thus in two seconds the gantry would make two 360° rotations and would acquire a single 10 mm slice. But to be clinically useful, the overall image series comprising the X-ray examination should encompass about 40 cm of the patient's abdomen. However acquiring a 40 cm image series at a rate of 10 mm in two seconds would take 80 seconds, far too long to continuously operate a mechanical gantry scanner without severe X-ray tube overheating. With a 30 second maximum continuous on time before overheating, a mechanical gantry system could make only 30 scans (e.g., one 360° scan/sec.) and acquire only about (30 sec./80 sec.)×40 cm≈15 cm of the abdomen, an insufficient span to be clinically useful.

In an attempt to make the best of a bad situation, a mechanical gantry CT scanner in helical mode is forced to move the patient laterally at approximately one slice width per 360° revolution of the gantry. Unfortunately, the reconstructed image will exhibit relatively poor signal to noise characteristics because the requisite 250 mAs is not met (e.g., each one second slice is the product of a one-second scan of 125 mA X-ray current, only 50% of the requisite 250 mAs for an abdomen image). Further, one 360° scan per each 10 mm slice represents a rather coarse pitch of 1:1, the pitch depicted in FIG. 2 in U.S. Pat. No. 4,630,202 to Mori. In addition, the mechanical gantry system operating in helical mode could only image 30 cm, whereas a 40 cm examination is typically required to be clinically useful.

This 1:1 coarse pitch gives rise to problems in reconstructing a CT image at each slice location. As is known to those skilled in the image reconstruction art, CT reconstruction assumes that the data to be processed are co-planar. However for image planes located between "turns" of the coarse 1:1 helix, actual data do not exist and must be interpolated from adjacent data points. Not only does this give rise to errors including artifacts in the images, but rather sophisticated data reconstruction techniques are required. In addition, the resultant rather poor quality image still represents a 30 second exposure, during which time there is contrast agent dissipation and body organ movement, further degrading utility of the image.

It is apparent from the foregoing that while helical mode scanning is considerably faster than conventional mode imaging, helical mode operation by a conventional mechanical gantry scanner has many deficiencies. As is set forth herein at the Detailed Description of the Invention, a scanning electron beam CT system can be operated in a helical mode to provide considerably faster imaging with a narrower or tighter pitch than is possible with a mechanical gantry system. However the narrow pitch and fast scanning repetition rate provided by such a system provide a faster stream of image data than can be economically stored in real time for later retrieval and processing.

There is a need for a real time method of processing or averaging data pertaining to an image slice provided by such a system. Preferably such a method should compress the slice image data to allow a smaller amount of compressed data to be stored and/or simultaneously processed to yield useful images. The present invention provides such a method. While directed primarily at helical mode scanning electron beam systems, the present invention may also be used advantageously with the slower mechanical gantry systems.

SUMMARY OF THE INVENTION

The present invention is a method and apparatus for processing in real time the data stream provided by a scanning electron beam CT scanner when used in a helical scan mode or a conventional mode. Of course the present invention can process the less voluminous stream of data provided by a mechanical gantry CT scanner system in conventional mode or, as described in U.S. Pat. No. 4,630,202 to Mori, in helical mode. The present invention includes a preferably high speed adder, and first and second memory banks, all in data communication with the data stream provided by the detector array in a scanning electron beam CT system, preferably operating in a helical scan mode. The helical scan has a helical pitch defined as the number (N) of electron beam scans for image slice, the pitch being four in the preferred embodiment.

On a first scan, the data stream enters the otherwise empty adder and is written into the first memory bank, substantially in real time. On the next scan, the contents of the first memory bank are summed with the new incoming data stream in the adder, the sum being written directly to the contents of the second memory bank, again substantially in real time. On the following scan, the new data are summed in the adder with the contents of the second memory bank (i.e., added to the sum of the data for the first and second scans), and the resultant is written to the first memory bank, overwriting any data previously therein. On the following scan, the contents of the first memory bank is summed in the adder with the new data corresponding to the fourth scan and the resultant data is stored in the second memory bank, and so on. After N scans, the contents of the last-written to memory bank (in the above example, the second memory bank) are divided by N to yield, essentially in real time, resultant average data corresponding to the image slice. In this fashion, the quantity of resultant data to be stored or further processed post-acquisition is reduced by a factor of N.

Other features and advantages of the invention will appear from the following description in which the preferred embodiments have been set forth in detail in conjunction with the accompanying drawings.

DESCRIPTION OF THE PREFERRED EMBODIMENTS

Figure 1:
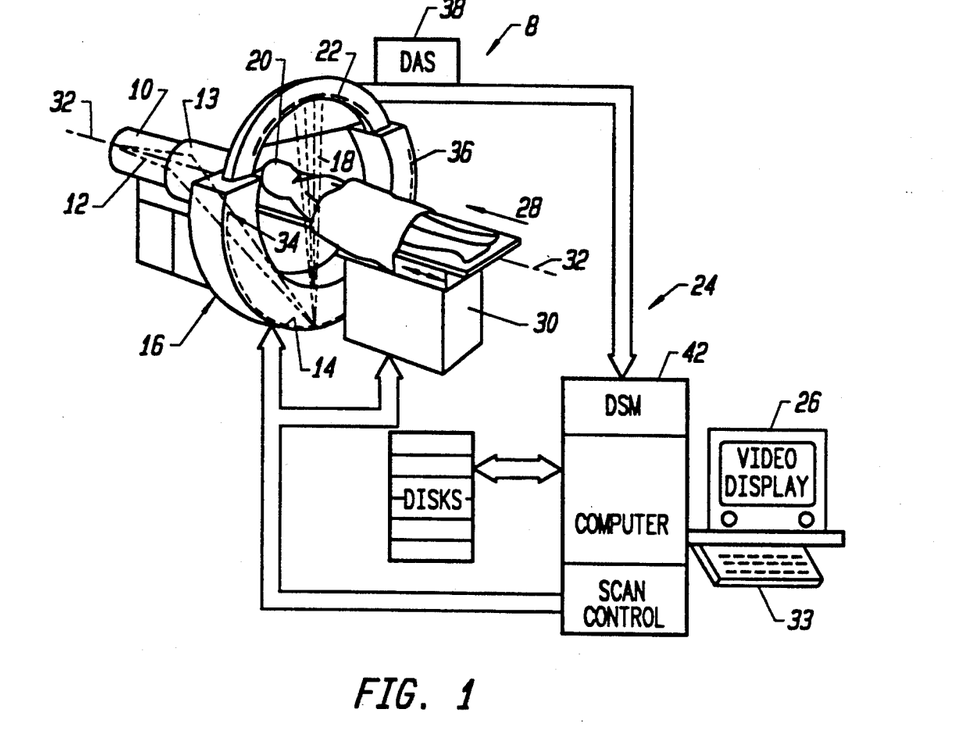
FIG. 1 depicts a scanning electron beam CT system operating in helical mode, the system including a real time data averager according to the present invention.

FIG. 1 depicts a scanning electron beam computed tomography ("CT") system 8 that can operate either in a helical mode or a conventional mode. System 8 includes a vacuum housing chamber 10 wherein an electron beam 12 is generated and caused by a beam optics assembly 13 to scan a circular target 14 located within chamber 12's front lower portion 16. Upon being struck by the electron beam, which typically scans 210° or so, the target emits a moving fan-like beam of X-rays 18 that pass through a region of a subject 20 (e.g., a patient or other object) and then register upon a region of a detector array 22 located generally diametrically opposite. The detector array outputs data to a computer processing system 24 that processes and records the data to produce an image of a slice of the subject on a video monitor 26. As indicated in FIG. 1, the computer system 24 also controls the system 8, and includes the present invention 42, a "DSM" or Data Acquisition System Memory.

Under control of an X-ray practitioner, computer system 24 can cause system 8 to operate in a conventional mode or a helical mode. In conventional mode, computer system 24 causes couch positioning mechanism 30 to laterally move patient 20 along the Z-axis in stop and go increments of typically about 1 mm to 10 mm, each increment taking about second to accomplish. As noted, in conventional mode, the electron beam scans while the patient 20 is stationary, between lateral movements. In helical mode, computer system 24 causes couch positioning mechanism 30 to operate continuously during electron beam scanning.

A scanning electron beam system such as that shown in FIG. 1 has several advantages over a mechanical gantry system. Because no moving parts are required to scan the electron beam, a single scan can take as little as 0.05 seconds, the beam 12 being caused to scan by the beam optics assembly 13. Further, because the production of the X-rays 18 occurs at the target ring 14 (typically a tungsten material), heat dissipation associated with X-ray production occurs over the relatively large target ring. As a result, the beam current associated with the electron beam 12 can be relatively high, e.g., 1,000 mA.

During helical mode scanning, the patient 20 is continuously moved laterally as indicated by arrow 28 by a couch drive mechanism 30 along the system Z-axis 32, under control of the computer system 24. (Arrow 28's direction could of course be reversed, as could the position of patient 20 atop mechanism 30.) As noted, this continuous lateral movement is in contrast to conventional mode scanning wherein the couch drive mechanism 30 advances the patient 20 along the Z-axis 32 in a "stop and go" fashion, scanning occurring only during the "stop" periods. Since each "stop and go" lateral repositioning of patient 20 can take one second, it will be appreciated that a helical scan mode provides a faster repetition scan rate than a conventional scan mode.

$$V \text{ (mm/sec)} = \frac{\text{Slice Width (mm)}}{N \times [\text{Time}_{single\ sweep} + \text{Time}_{flyback}]}$$

Typically in helical mode, couch drive mechanism 30, under control of computer system 24, moves the patient 20 laterally with a velocity V: where the slice width is typically the 1 mm to 10 mm image slice width determined by the X-ray practitioner, and N=number of electron beam scans per imaged slice width, and also represents the pitch, as determined by the X-ray practitioner controlling system 8. Couch drive mechanism 30 and its control by computer system 24 are well known to those skilled in the art of helical mode CT scanning, and will therefore not be described in further detail.

Figure 2:
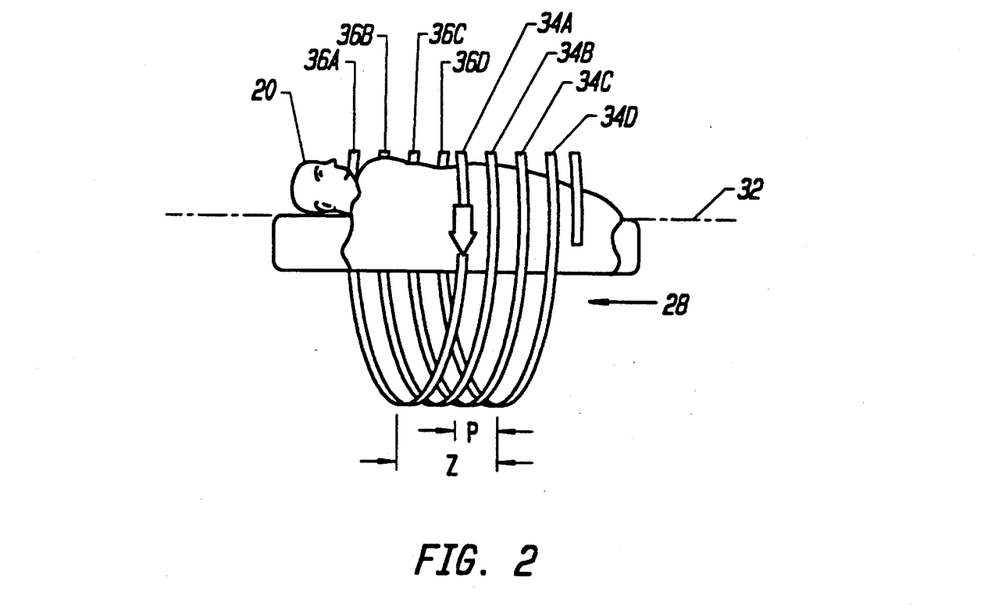
FIG. 2 is a schematic representation of a helical scan resulting from a system making four scan cycles per unit lateral slice displacement.

FIG. 2 illustrates the helical nature of the scan provided by system 8. In the scanning electron beam system 8 of FIG. 1, the electron beam 12 strikes target 14 at end 34, and scans in a generally circular arc until the other target end 36 is reached, the scan typically covering about 210°. Upon reaching end 36, the beam optics assembly 13 rapidly moves the beam 12 back to end 34 to start a new scan. In the preferred embodiment, a single 210° scan is accomplished in about 50 ms to 100 ms, with a flyback time of about 16 mS or less (e.g., the time wherein the beam 12 is relocated from target end 36 to target end 34). As is well known to those skilled in the imaging arts, an X-ray image may be reconstructed as long as the scan angle is at least 180° plus the width of the X-ray fan beam 18. In the system of FIG. 1, a 210° scan angle is sufficient to meet these requirements.

Depending upon the nature of the X-ray study undertaken, the computer system 24 causes couch mechanism 30 to move the patient 20 laterally a distance Z corresponding to the slice width of the X-ray image to be acquired, the slice-width being typically in the range of from about 1 mm to about 10 mm. Because the scanning electron beam system of FIG. 1 does not require mechanical movement of a gantry, system 8 typically can provide multiple (N) scan cycles per unit Z distance movement by the patient 20 along the lateral Z-axis 32. This capability is schematically represented in FIG. 2 by the four (N=4) helical scan cycles that occur for a given lateral displacement Z.

With reference to FIG. 2, assume that Z=10 mm, and that N=4, and that system 8 is required to provide a clinically useful 40 cm examination of patient 20's abdomen. This examination is made by acquiring 40 images, each of which is a slice 10 mm in thickness. As has been noted, 250 mAs dosage is required to satisfactorily image a human abdomen. If system 8 operates with, say, 650 mA beam current, the 250 mAs abdomen dosage requirement is fulfilled if a slice is scanned in 0.40 seconds. This requirement is easily met because system 8 can complete a single 210° scan in 50 ms to 100 ms and is typically fixed at a repetition rate corresponding to one of these repetition time durations. For example, if operated with a 100 ms scan time, system 8 could complete 4 scans in 0.40 seconds (e.g., N=4), while covering say 10 mm lateral abdomen distance with 650 mA electron beam current. A clinically useful 40 cm abdomen image will take about 18.6 seconds (e.g., 40 cm/(10 mm per slice)×4 scans/slice×0.116 second/scan). (In this example, the 0.116 second/scan represents a 100 ms scan time plus 16 ms flyback time; in a 50 ms scan time mode, flyback time is typically about 8 ms.) By suitably processing scan data from the detector array 22, the computer system 24 can produce images on display 26 corresponding to each scan slice, and where the scan pitch exceeds 1:1, data on intermediate planes can also be imaged.

Thus not only can the scanning electron beam system 8 image a 40 cm patient section in considerably less time that a mechanically rotating gantry system (thereby minimizing motion artifacts and contrast medium dissipation), but each of the 40 images results from a relatively narrow pitch (e.g., 4:1) and readily fulfills the minimum mAs dosage for an image to exhibit acceptable signal to noise ratio.

In system 8, the X-ray practitioner can readily change the value of N via keyboard 33, which is coupled to computer system 24. For example, the practitioner may select N=4 for an abdominal examination, N=8 for skull examination, etc. A higher value of N is necessitated by the minimum X-ray dosage required for the particular examination. Thus, since the bones in the human skull are relatively dense and absorb more X-rays than abdominal tissue, a tighter or narrower pitch (e.g., higher "N") is preferred for a skull examination as compared to an abdominal examination. With reference to FIG. 2, if the X-ray practitioner selects, say, N=4 and Z=10 mm, the computer system 24 will cause four 210° scans to be accomplished in the time it takes for the patient to be moved continuously 10 mm along the Z-axis by couch mechanism 30.

As is well known to those skilled in the imaging arts, a relatively narrow pitch, e.g., 4:1, greatly minimizes helical reconstruction artifacts in the reconstructed image. With reference to FIG. 2, such artifacts arise because the image data pertaining, for example, to a region of the patient's sternum corresponding to the start of the first scan, denoted 34A, will not precisely coincide with data for the same region 50 ms or 100 ms later when the same scan ends, denoted 36A. The discrepancy arises of course because during helical mode scanning, the patient 20 is continuously moving. The discrepancy is especially severe when the pitch is only 1:1 because the patient's continuous lateral movements mean the resultant slice does not represent a full data set. But as the pitch becomes tighter or narrower than 1:1, (e.g., N≧1) more actual data are acquired and the reconstruction artifacts lessen in magnitude, until at about N≧4 these artifacts are relatively unimportant.

Thus, in contrast to the coarse 1:1 pitch demonstrated in FIG. 2 in U.S. Pat. No. 4,630,202 to Mori, system 8 generates actual data corresponding to turns on the "helix" intermediate to the first and last scans 34A-36A and 34D-36D. With a pitch of 4:1, system 8 provides four times the number of data points to computer system 24, thereby enabling greater reconstruction accuracy. Unlike the coarse 1:1 pitch system illustrated in the Mori patent, there is no need for helical interpolation of data when, as here, a relatively large pitch is used. Thus, system 8 in FIG. 1 can reconstruct a 40 cm abdomen image from, say, 40 slices comprising 160 scans. Further, if sufficient data memory were available to store all of the image data, a scanning electron beam in a helical mode could be operated continuously for perhaps 60 seconds to image 60 cm, if required.

Thus, on one hand while a relatively tight pitch, e.g., 4:1 is desirable for high quality imaging, the sheer volume of data made available can be overwhelming. For example, if the detector array 22 includes say 864 X-ray detectors each of which samples the X-ray beam 864 times per 100 ms, 210° scan, the product represents 1.5 MB/scan (1,500,000 bytes/scan), or about 15 MB/second. Thus, the 40 cm abdominal examination described above represents the acquisition of 160 scans, which at 1.5 MB/scan produce about 240 MB of data in about 18.6 seconds, or a data stream of about 13 MB/sec. taking into account the flyback time during which no data is acquired.

Absent a real-time form of data compression, it simply is not feasible to consider a scanning electron beam CT system operating in a helical mode. Because of the 13 MB/sec data rate, at present the only feasible storage is relatively expensive high speed RAM, or extremely expensive parallel transfer disks. Further, even if such high speed storage were available, the quantity of the data to be stored is almost overwhelming, e.g., 240 MB per 18.6 second study. Known techniques for processing data from CT scanners are inadequate to keep up with the data stream that a scanning electron beam CT system operating in a helical mode can provide.

But for the present invention, element 42 on FIG. 1, system 8 would require an extremely large capacity of fast and expensive memory which, at best, would allow data storage for post-acquisition processing. Such a "solution" however would prevent the X-ray practitioner from learning in real time whether an acceptable image scan was attained.

With reference to FIG. 1 and FIG. 2, a Data Acquisition System or "DAS" 38 is preferably mounted adjacent the detector assembly 22. The DAS 38 provides signal processing including analog to digital conversion for the output signals from the approximately 864 detector units comprising assembly 38. Assembly 38 further includes a DAS TAXI 40 circuit that provides data transceive capabilities, preferably over two fiber-optic cables, between DAS 38 and the computer system 24.

Figure 3:
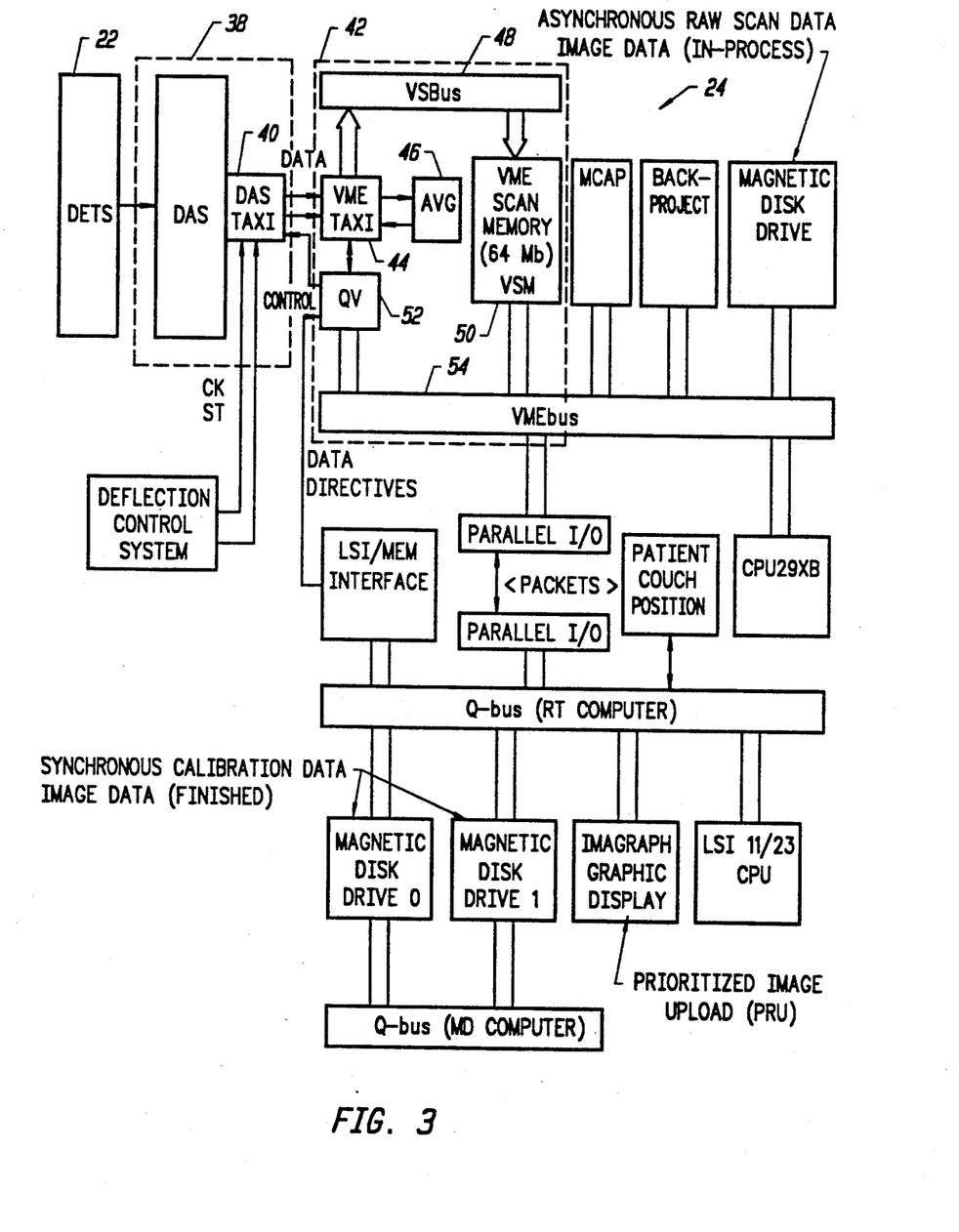
FIG. 3 is a simplified block diagram of computer system 24, showing data acquisition, reconstruction and storage according to the present invention 42.

At the receiving end of the fiber-optic cables, computer system 24 includes the present invention, a Data Acquisition System Memory or "DSM" 42. As shown in FIG. 3, DSM 42 includes a VME TAXI 44, a real-time averaging circuit "AVG" 46, a VSBus 48, a VME Scan Memory 50, a QV interface circuit 52, and functions provided by a VME bus 54. The remaining elements of computer system 24 shown in FIG. 3 primarily concern the post-acquisition display of X-ray images, using display 26 for example, as well as electron beam 12 displacement, patient couch mechanism 30 displacement, and selection of the scan pitch N.

Figure 4:
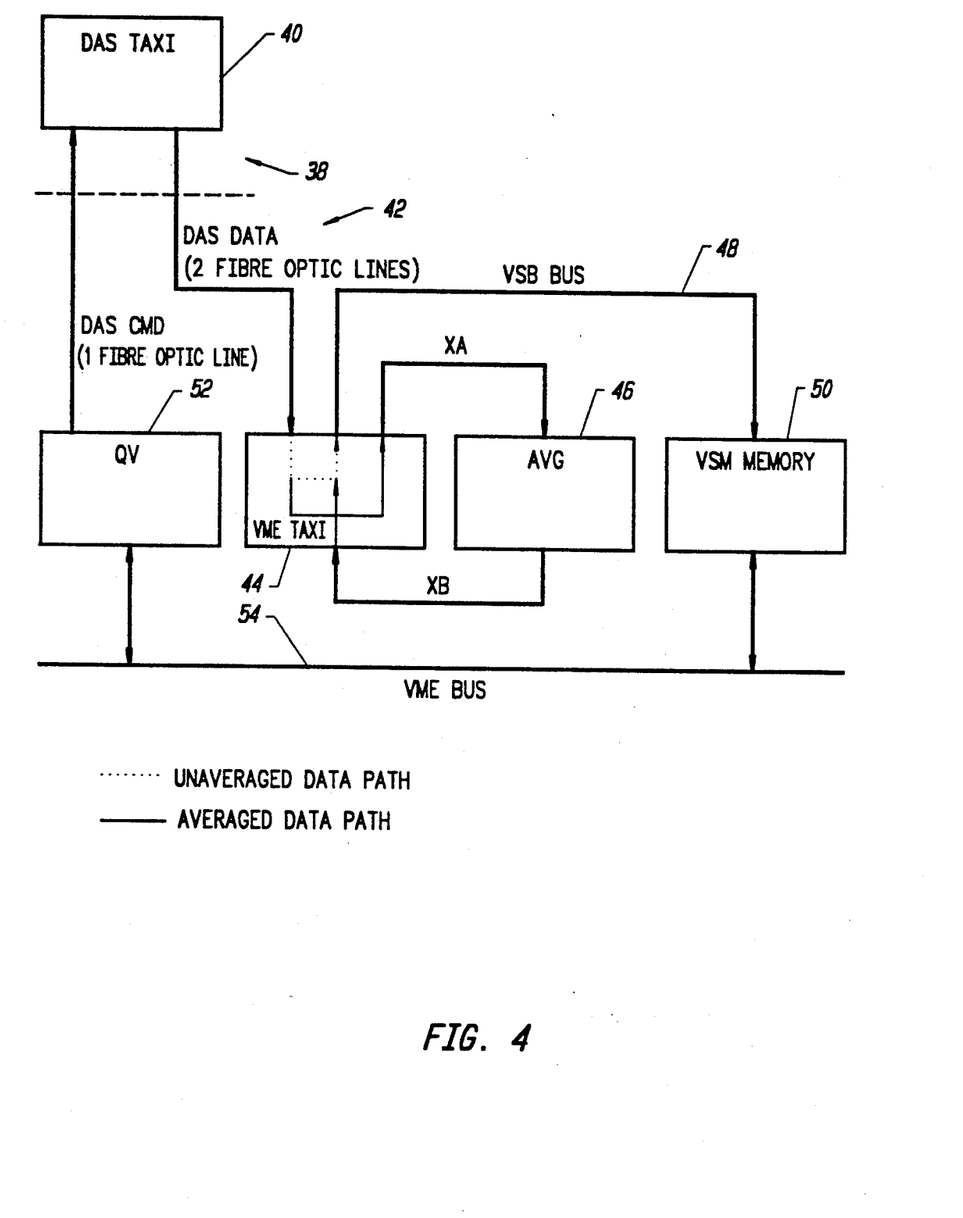
FIG. 4 is a block diagram showing the functional relationship between the VME scan memory components shown in FIG. 3.

FIG. 4 shows the data path and components comprising DSM 42. A stream of data from the DAS TAXI 40 is coupled, preferably via fiber-optic cable, to the VME TAXI 44. The VME TAXI 44 in turn diverts the raw incoming data stream to the AVG 46 circuit, and receives averaged data (to be described) from the AVG circuit 46. The VME TAXI 44 then sends the averaged data via the VSBus 48 to the VSM memory 50. The VME bus 54 communicates with the VSM memory 50 and the QV circuit 52 (see FIG. 5C). The primary function of the QV circuit 52 is to allow the X-ray practitioner operating system 8 to enable and to initiate a data acquisition sequence at the DAS 38. These enable and acquisition signals are sent from the QV, preferably through fiber-optics, back to the DAS TAXI 40. The VSM memory 50 is preferably high speed memory, such as four 16 MB boards configured to provide 64 MB of rapid storage. Preferably the VSM memory 50 receives data from the VME TAXI 44 as a pair of 16-bit words at an average rate of 138 ns/word. Preferably the data are written to VSM memory 50 as 32-bit longwords, where the VSM memory 50 has a maximum cycle time of about 240 ns/32-bit longword transfer. Other components having similar characteristics could also be used.

Figure 5A:
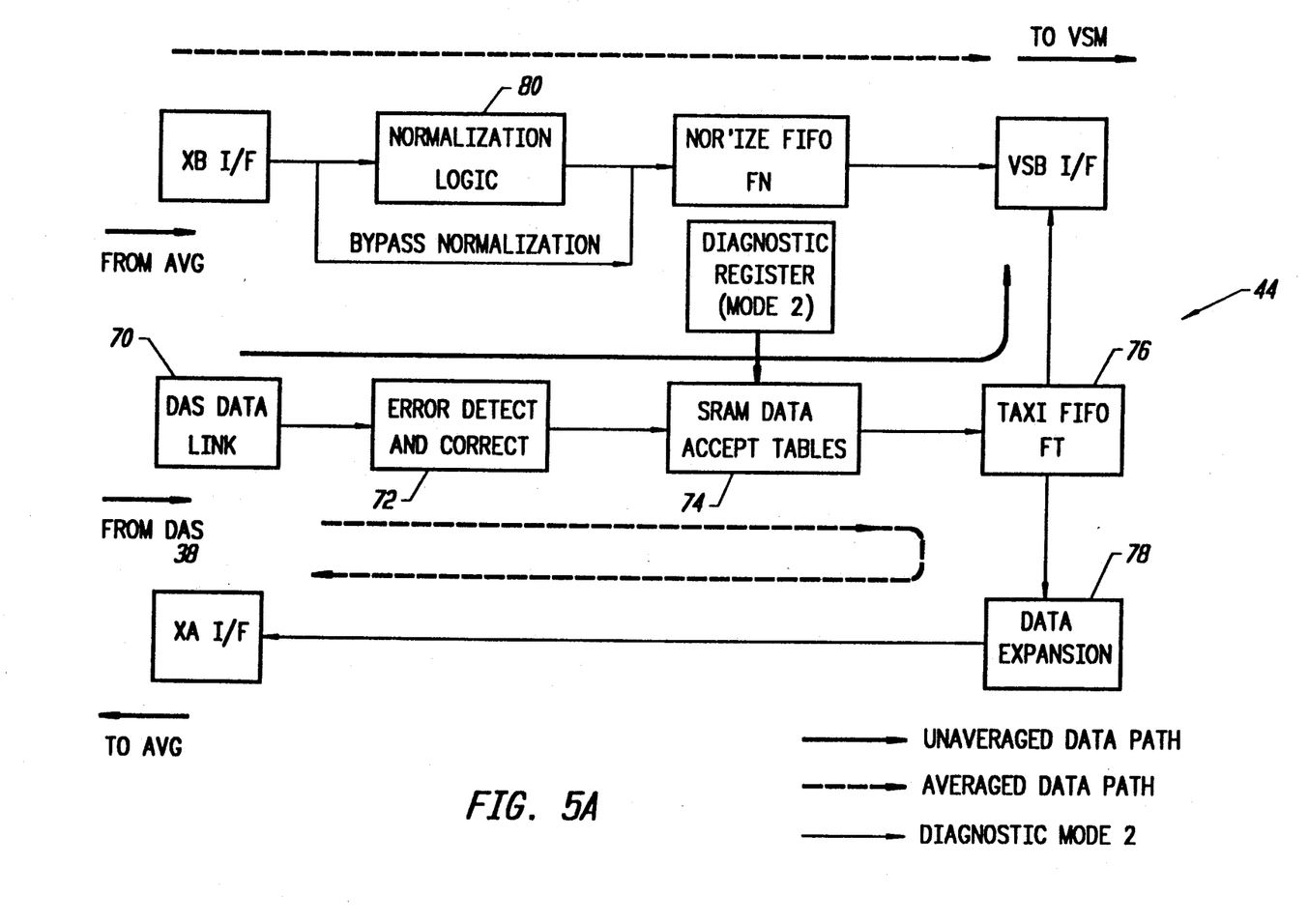
FIG. 5A shows in detail the elements comprising the VME TAXI circuitry shown in FIG. 3.
Figure 5B:
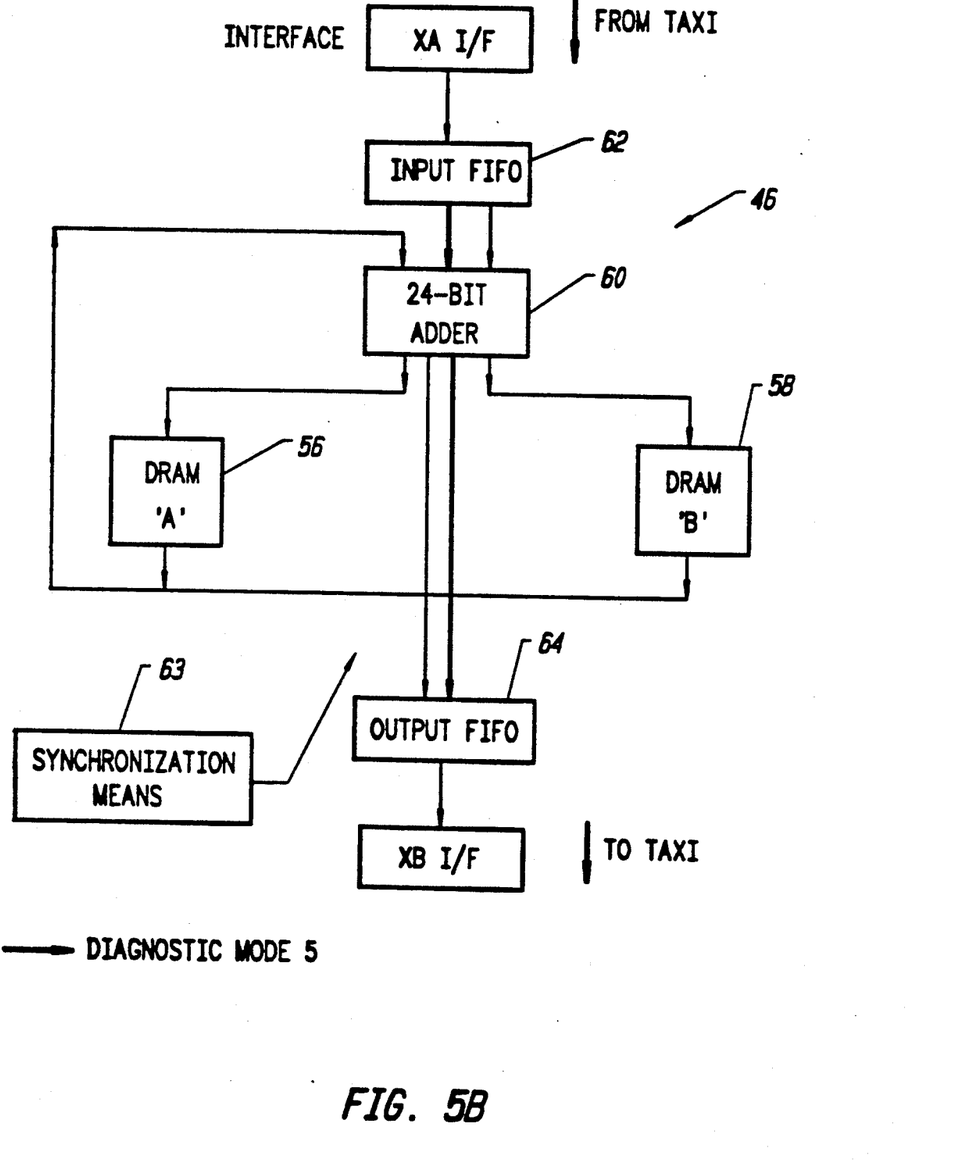
FIG. 5B shows in detail the elements comprising the AVG circuitry shown in FIG. 3.
Figure 5C:
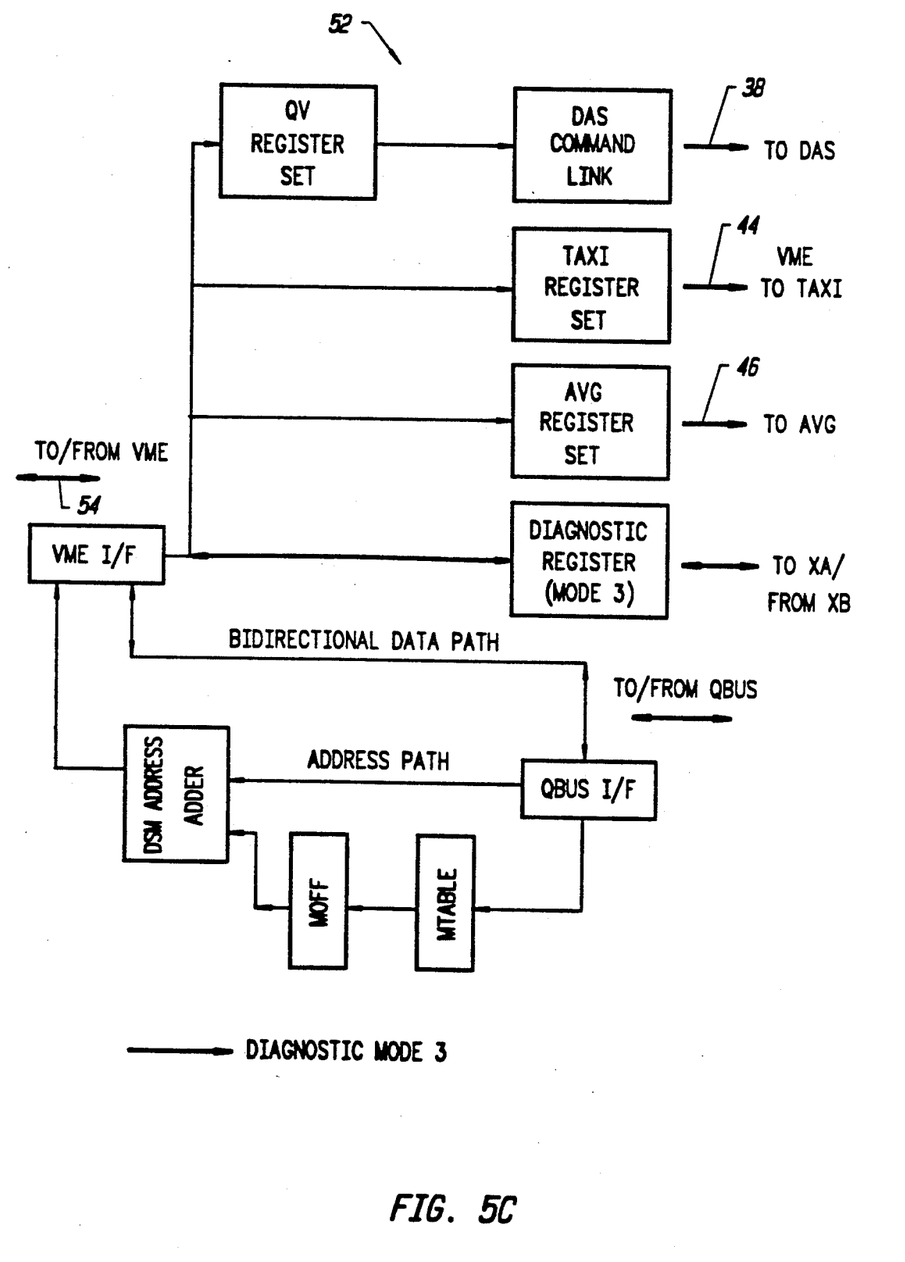
FIG. 5C shows in detail the elements comprising the QV circuitry shown in FIG. 3.

The VME TAXI 44 is depicted in FIG. 5A. As noted above, circuit 44 acts as a conduit both for averaged and for unaveraged data. Averaged data are provided by the real-time averager AVG circuit 46. As best seen in FIG. 5B, the AVG circuit 46 comprises first and second memory banks 56, 58 which, via a preferably 24-bit adder 60, are in data communication with the stream of data from DAS 38 corresponding to the output data from the detector array 22. Preferably memory banks 56, 68 are each 768k×24-bit high speed DRAM units. The AVG circuit 46 also includes a FIFO input register 62 coupled between the incoming stream of data and the input to adder 60. This FIFO register 62 essentially serves to time synchronize the data flow into the AVG circuit 46 with data transfers from memory banks 56, 58 into the 24-bit adder 60. Similarly an output FIFO register 64 serves to time synchronize data from the AVG 46 to the VME TAXI 44.

Data from the detector array 22 pass from the DAS 38 and the DAS TAXI 40, through the VME TAXI 44 into the AVG circuit 46, as shown in FIG. 4. FIG. 5A shows in detail the data path within the VME TAXI 44. As shown in FIG. 5A, the VME TAXI 44 provides error correction, time synchronization as well as data expansion unique to the specific implementation of applicant's system 8 and DSM 42. With reference to FIG. 5A, incoming DAS 38 data arrive as a pair of preferably 16-bit words transmitted serially via two fiber-optic cables. A DAS Data Link 70 converts the incoming data to parallel mode and passes the converted data to error detect and correct circuitry 72, wherein error detection and correction take place. The resultant data pass to an SRAM Data Accept Table 74, which, for the purposes of the present invention, merely passes the corrected data through to the TAXI FIFO FT 76. The TAXI FIFO FT 76 time synchronizes and passes the data as a pair of 16-bit words to a Data Expansion unit 78, which is unique to applicant's implementation of system 8. The DAS 38 data incoming to unit 78 are 16 bit-words that preferably include two gain bits and twelve data bits. Unit 78 serves to expand the twelve data bits to a twenty-four bit integer format for use in the AVG circuit 46.

The operation of the AVG 46 circuit will now be described. With reference to FIG. 5B, a synchronization circuit 63 comprising standard counters and PALs sequences the operation of data flow to and from the adder 60 and memory banks 56, 58. Essentially the synchronization circuit 63 tracks the number of system scans, i.e., 1, 2, N−1, N. For the first scan, circuit 63 causes input data to flow into the first memory bank 56 (although alternatively the first and second memory banks could of course be interchanged). For subsequent scans 2 through and including N−1, circuit 63 causes the output of whichever memory bank (56, 58) was last written and directs such output to the input of the adder 60. For the Nth scan, circuit 63 directs the output of adder 60 to the input of FIFO 64, the output of which FIFO 64 is then caused to pass to a divide by N, namely normalization logic 80 on VME TAXI 44 (see FIG. 5A). Because the design and implementation of synchronization circuit 63 is straightforward and known to those skilled in the art of logic design, further details are not given. In the following description, it will be assumed that data flow is synchronous, and the detailed operation of synchronization circuit 63, FIFO 62 and FIFO 64 will be ignored, and proper and synchronous data flow will be assumed.

Assume that system 8 is set to operate in helical mode with a 4:1 pitch, e.g., N=4 scans per image slice. Data from the detector array 22 corresponding to a first scan, scan 1, pass from the DAS 38 and the DAS TAXI 40 through the VME TAXI 44 into the AVG circuit 46. Within the AVG circuit 46, the data are written essentially in real time to the adder 60 and to the first memory bank 56.

During scan 2, data again passes from DAS 38 into the adder 60. Simultaneously the contents of the first memory bank 56 are also provided as input to adder 60, which adds the new incoming data to the data previously stored in memory bank 56. The resultant summation from adder 60 is written, essentially in real time, into the second memory bank 58, overwriting any contents therein. During the third scan, the incoming data stream from DAS 38 is summed by adder 60 with the contents of the second memory bank 58, and the new resultant sum is written essentially in real time into the first memory bank 56, overwriting any previous data therein. The first memory bank 56 will now contain the sum of the data sets representing the first plus the second plus the third scans. During the fourth scan, data from the DAS 38 is summed by adder 60 with the contents of the first memory bank, and the new resultant sum is written, essentially in real time, into the second memory bank 58, overwriting any previous data therein. The second memory bank 58 now contains the sum of the data sets representing the first, second, third and fourth scans.

Since, in this example, the X-ray practitioner has caused system 8 to scan a slice width with N=4 scans, as the data for the fourth scan are summed into adder 60, essentially simultaneously the contents of memory bank 58 are divided by N, or 4. This divided-by-N is accomplished by Normalization Logic 80 in VME TAXI 44. In the preferred embodiment, logic 80 converts the 24-bit integer sum from the AVG 46 back into a 16-bit averaged result, with 2 gain bits and 12 data bits. Normalization is a three step process: preshifting, shifting and rounding. Because such division techniques are known to those skilled in digital logic design, further details are not given here.

The net effect of the AVG 46 summation and the Normalization Logic 80 division is to create a running or "on-the-fly" real-time average value of data from the N (or in this case 4) scans comprising a single image slice. As shown in FIG. 3, this "averaged data" passes via the VME TAXI 44 through the VSBus 48 and is written into VSM memory 50. Note that because the AVG circuit 46 and VME TAXI 44 provide real-time averaging, the storage requirements for VSM 50 have been reduced by a factor of N, or four in this case. If, however, N had been 5, instead of dividing after four scans, data from the fifth scan would be added to the cumulative data for scans one through four, and the contents of the thus last-written to memory bank then divided by five.

While the above description has been made with reference to operation of a scanning electron beam CT system operating in helical mode, the present invention may also be used to real-time average data provided in a conventional mode of operation. Further, the present invention can also be used to provide real-time averaging of data obtained from a mechanical gantry system, such as described in the Mori patent, whether operated in conventional or helical mode. For example, the present invention could be used in lieu of Mori's data correction circuit 20. However because of the relatively slow acquisition rate associated with such mechanical gantry systems, the advantages provided by the present invention would be optional rather than a necessity (as in the case with scanning electron beam systems).

Modifications and variations may be made to the disclosed embodiments without departing from the subject and spirit of the invention as defined by the following claims. For example, while the preferred embodiment uses two memory banks 56, 58, more than two memory banks could also be used. Additional memory banks could, for example, provide redundancy, data correction and could provide a weighted profile whereby data from different scans are weighted differently in the summation.

What is claimed is:

1. In a computed tomography X-ray system, a method for providing real time analysis of data provided when X-rays generated by a system scan at least partially penetrate a subject and are detected by a detector array within the system, where data from N scans are to be averaged, the method comprising:
   (A) providing first and second memory banks, each bank capable of storing data representing one system scan; each bank having an input and an output;
   (B) providing means for adding;
      said means having a first input in data communication with data from the detector array, a second input in data communication with said output of said first memory bank, and a third input in data communication and with said output of said second memory bank;
      said means further having a first output coupled to said input of said first memory bank, a second output coupled to said input of said second memory bank, and a third output;
   (C) coupling a means for dividing by N to said third output of said means for adding, said means for dividing providing an output representing a division by N of its input data;
   (D) providing synchronization means for synchronizing data flow to and from said means for adding, said memory banks, said means for dividing by N, and for coordinating data flow therebetween;
   (E) for a first system scan, communicating data from the detector array corresponding to said first scan to said first input of said means for adding and essentially simultaneously writing said data into said first memory bank;
   (F) for subsequent system scans 2 through N−1, communicating data from the output of whichever of said first and second data banks was last written into an input of said means for adding essentially simultaneously with data communicated from the detector array corresponding to said system scan number 2 through N−1 to another input of said means for adding;
   (G) writing, into whichever of said memory banks was not last written to, essentially simultaneously the summation of said inputs present at scans 2 through N−1 from an output of said means for adding;
   (H) for system scan N, communicating data from the output of whichever of said first and second data banks was last written into an input of said means for adding essentially simultaneously with data communicated from the detector array corresponding to said system scan number N to another input of said means for adding;
   (I) providing a summation made by said means for adding at scan N to said third output of said means for adding;
   wherein the output of said means for dividing by N represents a substantially real-time average of data representing system scans 1 through N inclusive, and wherein the quantity of data representing system scans 1 through N to be subsequently stored or further processed is reduced by a factor of N.

2. The method of claim 1, whereby when N=2, steps (F) and (G) are omitted.

3. The method of claim 1, wherein said system is an scanning electron beam system.

4. The method of claim 3, wherein said system is operated in helical mode.

5. The method of claim 3, wherein said system is operated in conventional mode.

6. The method of claim 1, wherein said system includes a mechanically rotating gantry.

7. A computer tomography X-ray system, comprising:
   a moving electron beam that scans a stationary target that upon irradiation by said beam emits an X-ray fan;
   a detector array disposed generally diametrically opposite said target;
   a movable platform for holding an object to be examined intermediate said target and said detector array;
   said detector array detecting said X-ray fan after it passes at least partially through said object and providing a data signal proportional thereto;
   a computer processing system for processing data from said detector array to create therefrom an image of the X-rayed object;
   said computer processing system including a real time averager including:
   first and second memory banks, each bank capable of storing data representing one system scan, and each bank having an input and an output;
   means for adding;
      said means having a first input in data communication with data from the detector array, a second input in data communication with said output of said first memory bank, and a third input in data communication and with said output of said second memory bank;
      said means further having a first output coupled to said input of said first memory bank, a second output coupled to said input of said second memory bank, and a third output;
   a means for dividing by N, coupled to said third output of said means for adding, said means for dividing providing an output representing a division by N of its input data;
   synchronization means for synchronizing data flow to and from said means for adding, said memory banks, said means for dividing by N, and for coordinating data flow therebetween;
   said synchronization means for a first system scan, causing data to be communicated from the detector array corresponding to said first scan to said first input of said means for adding and essentially simultaneously writing said data into said first memory bank;

said synchronization means for subsequent system scans 2 through N−1, causing data to be communicated from the output of whichever of said first and second data banks was last written into an input of said means for adding essentially simultaneously with data communicated from the detector array corresponding to said system scan number 2 through N−1 to another input of said means for adding;

said synchronization means causing to be written into whichever of said memory banks was not last written to, essentially simultaneously the summation of said inputs present at scans 2 through N−1 from an output of said means for adding;

said synchronization means for system scan N, communicating data from the output of whichever of said first and second data banks was last written into an input of said means for adding essentially simultaneously with data communicated from the detector array corresponding to said system scan number N to another input of said means for adding;

said synchronization means causing to be provided a summation made by said means for adding at scan N to said third output of said means for adding;

wherein the output of said means for dividing by N represents a substantially real-time average of data representing system scans 1 through N inclusive, and wherein the quantity of data representing system scans 1 through N to be subsequently stored or further processed is reduced by a factor of N.

8. The system of claim 7, wherein said system is operated in a helical mode.

9. The system of claim 8, wherein said system is operated in a conventional mode.

* * * * *